US00PP23001P2

(12) United States Plant Patent
Kerley et al.

(10) Patent No.: US PP23,001 P2
(45) Date of Patent: Aug. 28, 2012

(54) ***LAVANDULA* PLANT NAMED 'KERLAVANGEM'**

(50) Latin Name: *Lavandula angustifolia*
Varietal Denomination: KERLAVANGEM

(76) Inventors: David Kerley, Cambridge (GB); Priscilla Grace Kerley, Cambridge (GB); Timothy Edward Kerley, Cambridge (GB)

( * ) Notice: Subject to any disclaimer, the term of this patent is extended or adjusted under 35 U.S.C. 154(b) by 310 days.

(21) Appl. No.: 12/661,870

(22) Filed: Mar. 25, 2010

(51) Int. Cl.
*A01H 5/00* (2006.01)

(52) U.S. Cl. ..... Plt./445

(58) Field of Classification Search ..... Plt./445
See application file for complete search history.

(56) References Cited

U.S. PATENT DOCUMENTS

PP9,119 P * 4/1995 Schofield ..... Plt./226

OTHER PUBLICATIONS

UPOV ROM GTITM Computer Database, GTI Jouve Retrieval Software 2011/10 Citation for 'KERLAVANGEM'.*

* cited by examiner

*Primary Examiner* — Wendy C Haas

(57) ABSTRACT

A new and distinct *Lavandula angustifolia* cultivar named 'KERLAVANGEM' is disclosed, characterized by little or no need to vernalize plants to induce flowering, with flowering beginning early in the season. Additionally, the new cultivar has broad flower spikes. moderately compact plant growth and broad foliage. The new variety is a *Lavandula angustifolia*, suitable for outdoor landscape and container use.

1 Drawing Sheet

Figure 1:
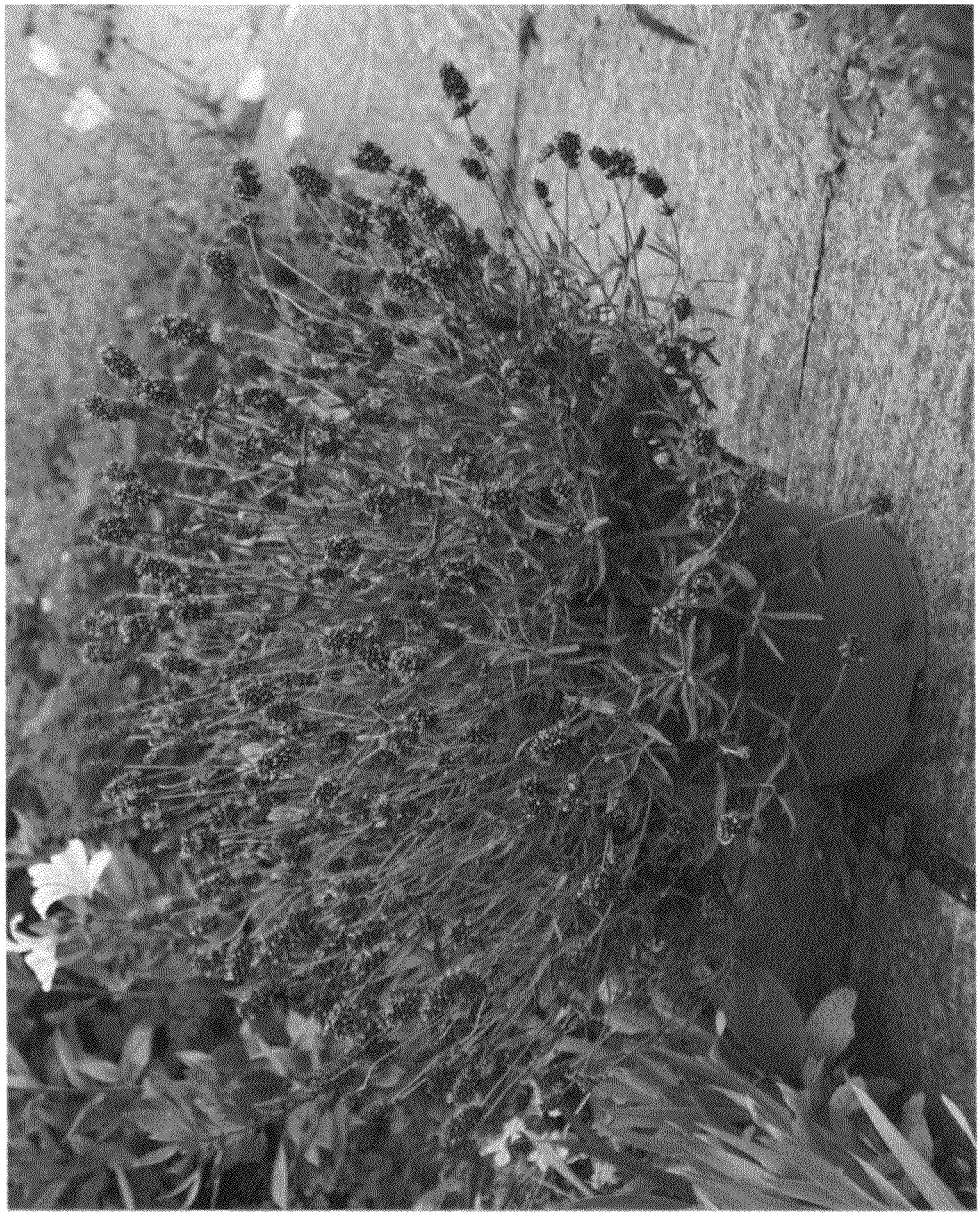

Latin name of the genus and species: *Lavandula angustifolia.*

Variety denomination: 'KERLAVANGEM'.

BACKGROUND OF THE INVENTION

The new cultivar is the product of a planned breeding program under the direction of the inventors, David Kerley, Priscilla Kerley and Timothy Kerley, all citizen of the United Kingdom. The objective of the breeding program was to produce new *Lavandula angustifolia* cultivars for commercial ornamental purposes. The breeding program consisted of organizing groups of unnamed, unpatented commercial *Lavandula angustifolia* varieties for open pollination. The seeds from these unnamed parents were collected and planted out, resulting in the selection of the new variety 'Kerlavagem' in the Spring of 2001. The breeding program and selection all took place at a commercial nursery in Cambridge, the United Kingdom.

Asexual reproduction of the new cultivar 'KERLAVANGEM' by vegetative cuttings was first performed in Cambridge, UK in the Autumn of 2001 and has shown that the unique features of this cultivar are stable and reproduced true to type in successive generations.

SUMMARY OF THE INVENTION

The cultivar 'KERLAVANGEM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERLAVANGEM' These characteristics in combination distinguish 'KERLAVANGEM' as a new and distinct *Lavandula* cultivar:

1. Little or no need to vernalize plants to induce flowering.
2. Broad flower spikes.
3. Flowering beginning early in the season.
4. Moderately compact plant growth.
5. Broad Foliage.

COMMERCIAL COMPARISON

Plants of the new cultivar 'KERLAVANGEM' are similar to plants of the unpatented variety *Lavandula angustifolia* 'Hidcote' in most horticultural characteristics, however, plants of the new cultivar 'KERLAVANGEM' produce consistently broader flower spikes on a thicker peduncle. Additionally, plants of 'KERLAVANGEM' do not require vernalization to induce flowering as required by 'Hidcote' and the new cultivar flowers earlier than 'Hidcote.' Plants of 'KERLAVANGEM' are more compact than 'Hidcote' and produce flowers with different colored pollen.

Plants of the new cultivar 'KERLAVANGEM' can also be compared to the commercial variety *Lavandula angustifolia* 'Blue Cushion' U.S. Plant Pat. No. 9,119. Plants of 'KERLAVANGEM' are similar to plants of 'Blue Cushion' in most horticultural characteristics, however, plants of the new cultivar have a darker flower color and flower spikes that are broader and occur on shorter, thicker peduncles. Additionally the new cultivar has a broader leaf than 'Blue Cushion' and does not require vernalization to induce flowering.

BRIEF DESCRIPTION OF THE PHOTOGRAPH

The accompanying photograph in FIG. 1 illustrates in full color typical plants of 'KERLAVANGEM' grown outdoors in Cambridge, UK. Plants are approximately 8 months old, shown in an approximately 4 inch container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'KERLAVANGEM' plants grown outdoors in Cambridge, UK. The growing temperature ranged from approximately 0 to 10° C. at night to 5 to 20° C. during the day. Measurements and numerical values represent averages of typical flowering types. No chemical or photoperiodic treatments were given.

Botanical classification: *Lavandula angustifolia* cultivar 'KERLAVANGEM.'

Age of the plant described: Approximately 8 months in an 11 cm pot.

PROPAGATION

Time to rooting: About 20 days at approximately 20° C.

Root description: Fine, well branched, becoming woody with age.

PLANT

Growth habit: Upright, slightly spreading, aromatic perennial.

Height: Approximately 20.5 cm.

Plant spread: Approximately 16 cm.

Growth rate: Moderate, approximately 60 cm in width after 3 years.

Branching characteristics: Moderate branching.

Diameter of lateral branches: Approximately 0.2 cm.

Texture of lateral branches: Moderately pubescent.

Internode length: Approximately 1 cm, quite variable.

Strength of stem: Strong.

Color of lateral branches: A color between RHS Yellow-Green 143A and Greyed-Green 191A.

Number of leaves per lateral branch: Approximately 12-16.

FOLIAGE

Leaf:

*Arrangement*.—Opposite, simple.

*Average length*.—Approximately 4.7 cm.

*Average width*.—Approximately 0.7 cm.

*Shape of blade*.—Narrowly oblanceolate.

*Apex*.—Acute.

*Base*.—Cuneate.

*Attachment*.—Sessile.

*Margin*.—Entire.

*Texture of top surface*.—Pubescent.

*Texture of bottom surface*.—Pubescent.

*Leaf internode length*.—Approximately 1 cm.

Color:

*Mature foliage upper side*.—A color between R.H.S. Yellow-Green 147A and 147B.

*Mature foliage under side*.—A color between R.H.S. Yellow-Green 147A and 147B.

*Venation*.—Type: One very prominent mid-vein, with a fine network of much smaller veins. Venation color upper side: Near R.H.S. Yellow-Green 147A and 147B. Venation color under side: Near R.H.S. Yellow-Green 144A.

Petiole: Not present.

FLOWER

Bloom period: Naturally blooming profusely late May through mid-Summer.

Inflorescence:

*Form*.—Small single flower in verticillasters arranged in spikes. Flowers have bracts. Corolla tube has 2 upper-lips and 3 lower lips.

*Flower spikes*.—Height: Approximately 3 cm. Diameter: Approximately 1.2 cm.

*Flower bud*.—Height: Approximately 0.5 cm. Width: Approximately 0.2 cm. Color: Near RHS Violet 89A and Violet-Blue 93A.

Individual flower:

*Corolla — length of upper lobes* (2).—Approximately 5 mm (hooded).

*Corolla — length of lower lobes*.—Approximately 3 mm.

*Corolla — width of upper lobes*.—Approximately 3.5 mm.

*Corolla — width of lower lobes*.—Approximately 2 mm.

*Shape of upper lobes*.—2 conjoined lobes.

*Shape of lower lobes*.—3 smaller lobes, fused for about half their len.

*Apex of upper lobes*.—Blunt, rounded.

*Apex of lower lobes*.—Mucronate.

*Texture of corolla — upper surface*.—Slightly savoyed.

*Texture of corolla — lower surface*.—Slightly savoyed.

*Color when opening — upper surface*.—Near RHS Violet 87B.

*Color when opening — lower surface*.—Near RHS Violet 87B.

*Color fully open*.—Near RHS Violet 87A and Violet-Purple 82A.

*Inflorescence bracts* (3 *buds subtend from each bract*) .—Approximately 5 mm wide×4 mm high.

*Bract color*.—Near RHS Greyed-Orange 165C, veins 165A.

*Calyx arrangement*.—Tube.

*Calyx width*.—Approximately 2-3 mm.

*Sepal length*.—Approximately 5 mm.

*Sepal texture*.—Very hirsute, hairs same colour as sepal.

*Sepal colour — flower opening*.—Near RHS Violet 86A, base near Yellow-Grey.

*Sepal colour — fully open*.—Near RHS Violet 86A, base near Yellow-Grey.

Peduncle:

*Peduncle length*.—Approximately 7.5 cm.

*Peduncle diameter*.—Approximately 1.5 to 2.0 cm.

*Aspect*.—Upright.

*Color*.—Near RHS Yellow-Green 147A.

REPRODUCTIVE ORGANS

Filament length: Approximately 1-1.5 mm.

Anther length: Approximately 0.5 mm.

Anther color: Near RHS Greyed-Orange 175C and 1.

Pollen color: Near RHS Greyed-Orange 167A.

Pollen amount: Sparse.

Pistil length: Approximately 6 mm.

Style length: Approximately 4 mm.
Style color: Near RHS White 155B.
Stigma color: Near RHS Violet 87D.

OTHER CHARACTERISTICS

Fragrance: Strong *Lavandula* scent, both flowers and foliage.
Low or no vernalization requirement: While most *Lavandula angustifolia* varieties known commercially require prolonged hours of low temperatures to induce flowering, 'KERLAVANGEM' flowers easily under conditions with very little cold treatment required.
Disease resistance: Neither resistance nor susceptibility to diseases or pests has been observed in this variety.
Drought tolerance and cold tolerance: Hardy perennial. Tolerates high temperature to at least 32° C. Tolerates low temperatures to −12° C. While specific drought tolerance has not been observed, once plants are established very little water is necessary to maintain plants.
Fruit/seed production: Fruit and seed production not observed.

What is claimed is:

1. A new and distinct cultivar of *Lavandula* plant named 'KERLAVANGEM' as herein illustrated and described.

* * * * *